United States Patent
Katz et al.

(10) Patent No.: US 7,153,264 B2
(45) Date of Patent: Dec. 26, 2006

(54) APPARATUS AND METHOD FOR IDENTIFYING SLEEP APNEA

(76) Inventors: Richard A. Katz, 11 Winthrop Dr., East Lyme, CT (US) 06333; Jeffrey S. Hall, 10 Ripple La., North Kingstown, RI (US) 02852; Albert H. Nuttall, 23 Coult La., Old Lyme, CT (US) 06371-0401; Tracey A. Dodenhoff, 525 Mendon Rd., North Attleboro, MA (US) 02760; Douglas Sawyer, 542 Walcott St., Pawtucket, RI (US) 02861

( * ) Notice: Subject to any disclaimer, the term of this patent is extended or adjusted under 35 U.S.C. 154(b) by 0 days.

(21) Appl. No.: 11/151,685

(22) Filed: Jun. 13, 2005

(65) Prior Publication Data

US 2006/0107954 A1 May 25, 2006

Related U.S. Application Data

(60) Provisional application No. 60/579,976, filed on Jun. 14, 2004.

(51) Int. Cl.
*A61B 5/00* (2006.01)
*A61B 5/02* (2006.01)
*A61B 5/08* (2006.01)

(52) U.S. Cl. .................. 600/300; 600/508; 600/529

(58) Field of Classification Search ............ 712/12
See application file for complete search history.

(56) References Cited

U.S. PATENT DOCUMENTS

| | | | |
|---|---|---|---|
| 5,285,793 A | * | 2/1994 | Slovut et al. ............ 600/519 |
| 5,769,084 A | | 6/1998 | Katz et al. |
| 5,995,742 A | * | 11/1999 | Jannson et al. ............ 703/21 |
| 6,381,559 B1 | | 4/2002 | Huang |
| 6,580,944 B1 | | 6/2003 | Katz et al. |
| 6,738,734 B1 | | 5/2004 | Huang |
| 6,942,626 B1 | * | 9/2005 | Salisbury et al. ........ 600/538 |
| 2003/0033094 A1 | | 2/2003 | Huang |

OTHER PUBLICATIONS

Huang, Norden E. et al, The Empirical Mode Decomposition And The Hilbert Spectrum For Nonlinear And Non-Stationary Time Series Analysis, Proc. Roy Soc. London, pp. 903-995, © 1998.

Huang, Norden E. et al, (Abstract)—A New View of Nonlinear Waves; The Hilbert Spectrum, Annual Review of Fluid Mechanics, Jan. 1999.

(Continued)

*Primary Examiner*—Charles A. Mamor, II
*Assistant Examiner*—Patricia Mallari
(74) *Attorney, Agent, or Firm*—Fleit Kain Gibbons Gutman Bongini & Bianco; Paul D. Bianco; Martin Fleit

(57) ABSTRACT

A method is provided for identifying a disease of a patient. The method includes collecting data of at least one cardio-respiratory function of the patient over time, eliminating artifacts from the collected data to create a new data record, constructing a phase-space from the new data record, and constructing a hypercube covering the phase-space. The method further includes calculating threshold criteria for quantifying dispersion characteristics of an attractor of the phase-space and determining the patient's tendency towards the disease based on the threshold criteria.

20 Claims, 11 Drawing Sheets

OTHER PUBLICATIONS

Katz Richard A., Chaotic Circuits for Communication, International Society for Optical Engineering, vol. 2612, Oct. 1995.

Analyze Nonlinear Non-Stationary signals with Hilbert Huang Transform, Web site—http://techtransfer.gsfc.nasa.gov/hht/hht/htm.

Superior Algorithms for Analyzing Nonliner Non-Stationary Data Web site—http://techtransfer.gsfc.nasa.gov/hht/attachments/hht-brochure-med.ptf.

Huang W. et al., Engineering Alalysis of Biological Variables: An Example of Blood Pressure Over 1 Day, vol. 95, pp. 4816-4821, © Apr. 1998 By The National Academy of Science.

Huang W. et al., Use of Intrinsic in Biology: Examples of Indicial Response of Pulmonary Blood Pressure To Step ± Hypoxia, vol. 95, pp. 12766-12771, © Oct. 1998 By The National Academy of Science.

* cited by examiner

APPARATUS AND METHOD FOR IDENTIFYING SLEEP APNEA

CROSS-REFERENCE TO RELATED APPLICATION

The present application claims priority to U.S. provisional patent application No. 60/579,976 filed Jun. 14, 2004. The provisional application is hereby incorporated by reference.

STATEMENT REGARDING FEDERALLY SPONSORED RESEARCH OR DEVELOPMENT

Research and development leading to the invention was performed under NCRADA-NUWCDIVNPT-02-129.

FIELD OF THE INVENTION

The present invention relates generally to the diagnostic of respiratory, cardiac, cardio-respiratory, and neurophysiological diseases, and more specifically it relates to an apparatus and method for determining sleep apnea.

BACKGROUND OF THE INVENTION

A number of epidemiological studies have shown that sleep apnea is a common disorder. Over 25 percent of apparently healthy adults over age 55 demonstrate sleep disordered breathing when screened at home. Moreover, within the pediatric, infant, and newborn population, the incidence of Apparent Life Threatening Event (ALTE), Sudden Infant Death Syndrome (SIDS), and sleep disordered breathing has also been well defined.

Sleep apnea's major symptom is excessive daytime sleepiness, and one physiological marker that predicts its existence is the presence of nighttime snoring. Excessive daytime sleepiness as a result of chronic sleep disordered breathing might be responsible for up to 50% of work related disability payments and 13% of all motor vehicle accidents. These and other statistics could support the fact that uncontrolled sleep apnea approaches a public health issue and the under-diagnosis of sleep apnea in the general population continues to exist.

In the overwhelming majority of those patients suffering from sleep-disordered breathing, the site of the apnea occurs within the upper airway. The recording of physiological measurements at night that documents airflow limitation is the currently accepted method to confirm the existence of sleep disordered breathing. This method is known as a polysomnography and is generally both time-consuming and costly.

While a polysomnography is suitable for the particular purpose to which it addresses, it is not suitable for the rapid identification of sleep disordered breathing while the patient is awake. Also, a polysomnography requires significant resources to perform. Generally, it is conducted in special facilities. A patient is located in one room for the night and typically arrives about 8:00 pm and leaves about 6:00 am. At least two trained technicians are present for the duration of the test. The technicians attach various sensors to the head, chest, arms and legs and then monitor various signals from the patient. The results, as multichannel charts and observed events, are then reviewed by one or more physicians of different specialties in order to determine the existence of sleep apnea or other respiratory dysfunction conditions. Furthermore, a polysomnography is labor intensive, requiring copious training and preparation. Also, it is uncomfortable and unpleasant for the patient, and often times, delivers inaccurate results due to the discomfort.

Given the obstacles of current sleep disorder diagnosis, the evolution of cardio-respiratory tools and techniques will need to be time sensitive, cost effective, and patient friendly while providing an accurate diagnosis, which in turn will allow better treatment to more patients. Overcoming these obstacles, the present invention is an apparatus and method for rapidly identifying respiratory, cardiac, cardio-respiratory, and neurophysiological diseases while the patient is awake.

SUMMARY OF THE INVENTION

The present invention is a novel signal processing method using higher dimensional phase-space construction obtained from one-dimensional scalar time series measurements from one or a number of physiologic variables such as nasal pressure, nasal temperature, chest-wall and abdomen expansion and contraction, ECG, EEG, EMG, etc. Primarily, the present invention relates to the measurement of nasal pressure for identifying sleep apnea, but the methodology has wide-ranging applicability to other areas of medicine beyond respiratory physiology, such as neuroscience (EEG, EMG) and cardiology (heart rate, ECG).

Specifically, the phase-space dynamics which define the present invention are (a) the measure of deflection from state to state of the fiducial trajectory as time advances—this measure is called the differential radius; (b) the particular (spatial) region of the phase-space attractor where the highest density of points are aggregated; (c) the degree of dispersion of neighbors surrounding this high density zone; and (d) the shape of the attractor. In the above, the attractor is defined as the spatial zone where all the points in the phase-space are aggregated. These measures (a,b,c, and d) are obtained using the Differential Radius, in combination with the KAHUNA hypercube, to ascertain quantitatively whether or not a patient is afflicted with sleep apnea. The methods of the present invention are derived from the theories of nonlinear dynamics and chaos. The nonlinearly processed time series provide clinical markers for the diagnosis and screening of patients subject to respiratory, cardiac, and other physiological dysfunctions.

Quantification of phase-space dynamics, and more specifically, deflection of trajectories away from the normal fiduciary orbits, identification of spatial regions or zones where orbiting points on the "attractor" most frequently visit or cluster, the dispersion about these cluster regions, and the shape of the attractor, all serve to quantify the phase-space dynamics, as the basis for diagnosing the presence of a physiologic disorder (e.g., apnea) over a short time interval (e.g., less than 20 minutes). Moreover, the measured time series, from which the phase-space orbits are generated, are derived from physiologic recordings that are gathered during the daytime while the patient is awake.

These nonlinear data processing methods provide new uses for aiding the clinical diagnosis, screening, treatment, and management of cardio-respiratory diseases. The methods and devices of the present invention are useful for precise detection and daytime monitoring of physiologic variables, particularly respiratory dysfunctions associated with a disorder known as obstructive sleep apnea (OSA). The device provides daytime detection, diagnosis and screening of physiologic dysfunction by nonlinear processing of time sequences of daytime sleep apnea recordings, principally (1) nasal pressure; but also other physiologic variables as well, such as (2) nasal temperature; (3) chest-wall resistance; (4) abdominal expansion-contraction; (5) oxygen saturation; (6) electrocardiogram (ECG); (7) heart rate (HR); and others.

The nonlinear algorithms, once applied to these physiologic variables, provide daytime diagnostic and screening indicators of dysfunction of a physiologic condition that is undetected by conventional methods used in the practice of sleep medicine. The results are determined immediately and can be presented to the patient by the attending physician as soon as the test is completed.

In accordance with one aspect of the present invention, there is provided a method for identifying a disease of a patient. The method includes the steps of collecting data of at least one cardio-respiratory function of the patient over time, eliminating artifacts from the collected data to create a new data record, and constructing a phase-space from the new data record. The method also includes the steps of constructing a hypercube covering the phase-space, calculating threshold criteria for quantifying dispersion characteristics of an attractor of the phase-space, and determining the patient's tendency towards the disease based on the threshold criteria.

In accordance with another aspect of the present invention, a method for identifying the disease of the patient includes the steps of collecting data of at least one cardio-respiratory function of the patient over time, constructing a first phase-space from the collected data, and calculating differential radii of the collected data in the first phase-space. The method also includes determining a threshold crossing level, calculating a percentage of differential radii exceeding the threshold crossing level, and preliminarily determining the patient's tendency towards the disease based on the percentage of differential radii. The method further includes eliminating artifacts from the collected data to create a new data record, constructing a second phase-space from the new data record, and constructing a hypercube covering the second phase-space. Finally, the method includes calculating threshold criteria for quantifying dispersion characteristics of an attractor of the second phase-space and determining the patient's tendency towards the disease based on the threshold criteria.

The disease to be identified may be Sudden Infant Death Syndrome, Apparent Life Threatening Event, sleep disordered breathing, respiratory disease, cardiac disease, cardio-respiratory disease, neurological disease, or similar disease.

The step of collecting data may be performed while the patient is awake and may be performed for approximately 15 to 20 minutes. The collected data may be of nasal temperature, chest-wall expansion and contraction, abdomen expansion and contraction, electrocardiogram (ECG), electroencepthalogram (EEG), electromyography (EMG). In an exemplary embodiment, the data may be of nasal pressure and may be collected approximately 10 times each breathing cycle.

In accordance with a related aspect of the present invention, the step of eliminating artifacts for the collected data may include truncating and interpolating the collected data. Namely, the data may be normalized, and any data outside a threshold range may be eliminated. The threshold range may be equivalent to 3.5 standard deviations. Furthermore, the eliminated data may be replaced with a linear interpolation of data within the threshold range.

The step of constructing the phase-space may include creating a multi-dimensional set of vectors. The creation of the set of vectors may include selecting a delay parameter and an embedding dimension. The delay parameter may be about 15 for a three dimensional set of vectors. The embedding dimension may be in the range of approximately 3 to about 6.

In accordance with another related aspect of the present invention, the step of constructing a hypercube includes creating a plurality of mini-cubes. The plurality of mini-cubes may be non-overlapping, and each mini-cube may be of substantially equal proportion. The number of mini-cubes may be in the range of approximately 512 to about 9,261. The plurality of mini-cubes may identify the highest density region of points within the phase-space. The plurality of mini-cubes may also quantify dispersive characteristics of the attractor and quantify the shape of the attractor.

The step of calculating the threshold criteria may include using the new data record in the calculation. The calculation may also include determining a minimum acceptable percentage of a number of data that pass through a specific mini-cube of the hypercube with respect to the number of data that pass through a mini-cube having the maximum density of data. The calculation of the threshold criteria may further include determining the minimum number of mini-cubes for the minimum acceptable percentage. A lower threshold criteria may indicate a tendency toward the patient having the disease.

In accordance with a related aspect of the present invention, the method of identifying the disease of the patient may be at least partially performed using a computer. The collection of data may be performed using signal processing hardware. The processing hardware may be a USB device that interfaces with a patient respiratory/cardiac measuring device and a microprocessor. The microprocessor may be a desktop or laptop computer.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2b is an expanded view of a segment of FIG. 2a;

DETAILED DESCRIPTION OF THE INVENTION

Figure 1:
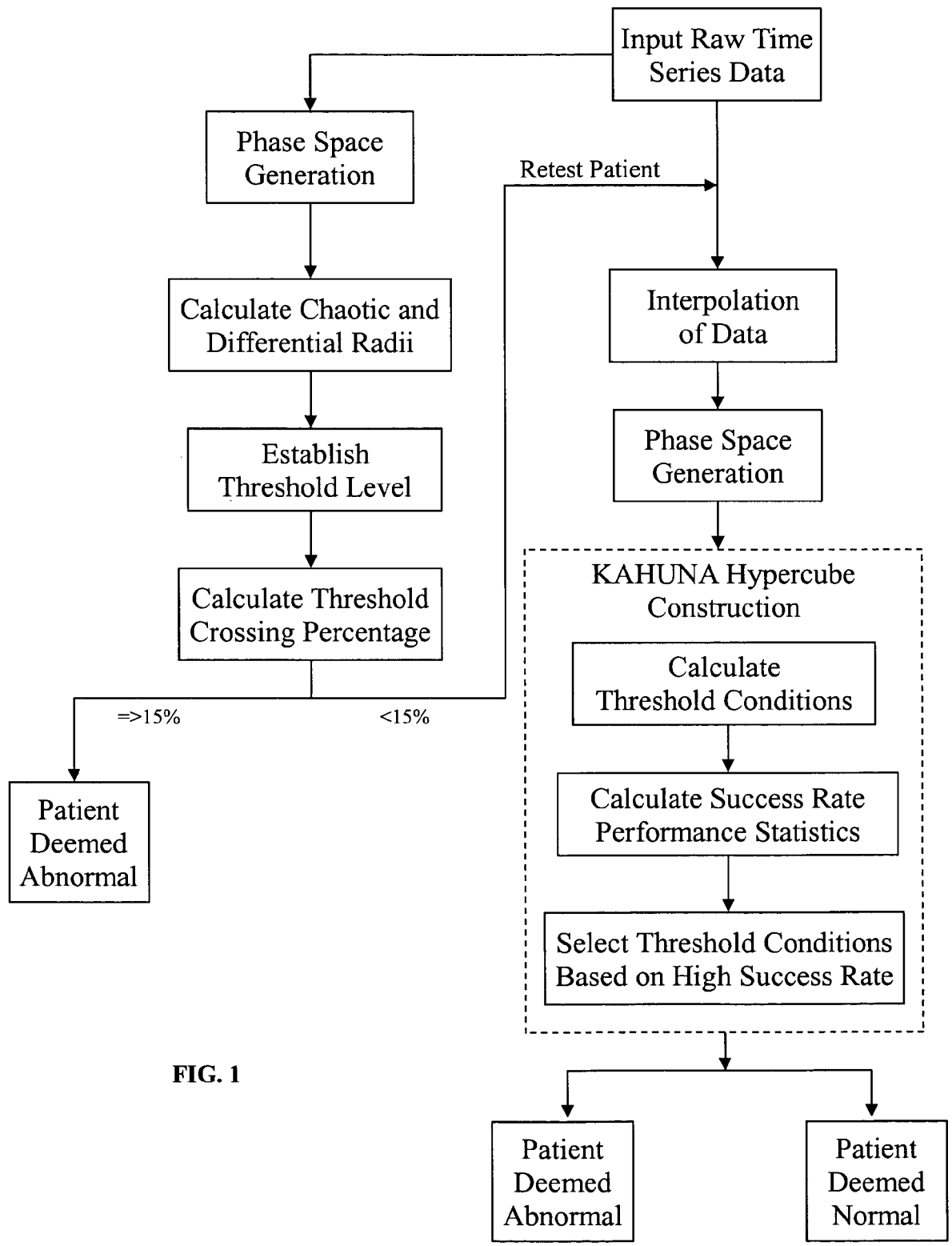
FIG. 1 is a block diagram representing a method for identifying sleep apnea.

The KAHUNA algorithm of the present invention, in combination with the Differential Radius technique for obtaining accurate automated classification of sleep apnea in which physiological data are collected and automatically scored during a short daytime interval, represents a novel approach to sleep research and clinical diagnosis in three significant areas: (a) testing can be performed during the daytime while the patient is in an awake state as opposed to nighttime while the patient is asleep; (b) testing can be performed over a short time interval of minutes as opposed to several hours; and (c) scoring of the test is done automatically in a matter of seconds.

Also, other features that relate to the invention and can be used with the invention have been set forth in U.S. Pat. Nos. 6,580,944 B1 and 5,769,084, and U.S. Patent Publication No. 2005/0020930, the contents of which are incorporated by reference herein.

The automatic screening and diagnostic device and method of the present invention apply nonlinear dynamical systems techniques not only to sleep apnea, but also to cardiological applications (e.g., fibrillation), neurological diseases (e.g., tremor), as well as any clinical situation in which nonlinearity in the physiology plays a significant role.

Additional uses of the present invention include pre-screening for otherwise hidden pathologies of patients undergoing anesthesia, monitoring young infants for life threatening cardio-respiratory disorders such as Sudden Infant Death Syndrome (SIDS), and pre-screening of professionals in industrial and military settings, such as truckers, airline pilots, and combat personnel, to mention a few.

In this respect, before explaining at least one embodiment of the invention in detail, it should be understood that the invention is not limited in its application to the details of construction and to the arrangements of the components set forth in the following description or illustrated in the drawings. The invention is capable of other embodiments and of being practiced and carried out in various ways. Also, it should be understood that the phraseology and terminology employed herein are for the purpose of the description and should not be regarded as limiting.

FIG. 1 illustrates a block diagram representing the method of the present invention. Raw time series data are obtained from a patient undergoing testing for sleep apnea. From these time series measurements, phase-space dynamics may be reconstructed. Once the appropriate phase-space parameters are established, the digital time record of measurements can be applied to generate the chaotic and differential radii. Once a threshold level has been established, the percentage of differential radii crossing the threshold is calculated. For a percentage of 15 or greater, the patient is deemed abnormal, i.e. having sleep apnea. If the percentage is less than 15, the raw time series data for the patient are retested using the KAHUNA hypercube.

Since the KAHUNA hypercube is sensitive to extreme spiking in the data record, an interpolation procedure can be invoked on the raw time series record. The interpolated data is then used during the generation of phase-space dynamics. Once the phase-space parameters are established, the KAHUNA hypercube is constructed. Construction of the hypercube involves the computation of threshold conditions and computation of success rate performance statistics. Based on high success rate statistics, certain threshold conditions are selected. From these selected threshold conditions, it is deemed whether a patient is normal or abnormal.

Digital Sampling of Raw Physiologic Time Series and Removal of Artifacts

From the raw physiologic time series measurements obtained from the nasal pressure transducer, for example, a measurement signal may be obtained in which the true nonlinear dynamics are preserved within the digital data that is collected. For purposes of nonlinear data processing, sampling of the collected data is typically done at 5 to 10 times (and sometimes even higher than) that which is typically used for sampling linear signals. For linear signal processing, the rule of thumb is to sample the data at 2 to 2.5 times the upper limit of the physical oscillation cycle, based on the Nyquist sampling theorem.

As normal breathing in human subjects generally occurs at an average rate of 15 times per minute, a linear sample rate of 8 Hz to 10 Hz would be sufficient (e.g., 2×4 Hz to 2.5×4 Hz). For nonlinear analyses, sampling at approximately 10 times each breathing cycle, or 40 Hz, is required to obtain useful results. This concept is made clear by observation of harmonics and intermodulation products that are visible in the temporal power spectra of various classes of nonlinear signals. For example, in order to observe a 3rd or 4th harmonic in such spectra, the data would need to have been sampled at a minimum of 3 or 4 times the fundamental frequency, respectively, to be visible in the spectrum in the first place. So, the Nyquist criterion no longer applies to nonlinear signals. Therefore, the detection device of the present invention was deemed to operate effectively based on a data sampling rate of 40 Hz (10 times the normal breathing cycle), and the 40 Hz sampling rate was implemented into the design of the device.

Often, during the collection of the measurement time series, large intermittent spiking (both positive and negative) appears in the data record. It is not always clear whether or not such transient spiking is real physiology being measured or simply an artifact of the data collection procedure, i.e. collection system generated noise, erratic and unintentional movement of the subject or of the measuring apparatus, to mention just two possibilities. The present invention provides a means of minimizing if not eliminating the effects of artifacts (i.e., non-physiological signals) being introduced into the physiologic data collection record by a procedure which involves truncation and interpolation.

Since the Differential Radius (DR) computation is minimally affected by artifacts in the data record, computation of the DR is based on the raw (uninterpolated) time series. However, the KAHUNA hypercube (described below) is highly sensitive to extreme spiking in the data record, and therefore the truncation-interpolation procedure can be invoked on the raw time series record prior to (phase-space) construction of the KAHUNA hypercube.

The truncation-interpolation procedure is performed in the following manner. First, the original data record is normalized by producing (without loss in generality) a new record of zero mean and unit variance. Namely, from the original data record, the sample mean is subtracted out, and this result is divided by the sample standard deviation. Next, variations in the data above a threshold of plus-or-minus 3.5, the equivalence of 3.5 standard deviations, are noted. Points crossing this threshold are eliminated.

There are several options for eliminating undesirable points: (a) truncate the crossover points and shorten the data record accordingly; (b) truncate the points and fill in the missing points with zero values, thereby preserving the original length of the data record; (c) preserve the original data record and replace the truncated points with a maximum value just below the 3.5 threshold or with the minimum value just above the −3.5 threshold; and (d) fill in the deleted points with a linear interpolation of points between the closest (good) data points within the threshold.

In one exemplary embodiment, the present invention utilizes strategy (d) for the following reasons. Option (a) was not selected because truncating the original record length was not as genuine as keeping the record length the same as the original one. In phase-space dynamics, padding a time sequence with zeros is equivalent to unnaturally stabilizing a system. Therefore, this eliminated option (b). Likewise, maximizing points in phase-space, option (c), seemed equally unnatural. Consequently, option (d) remained.

Figure 2A:
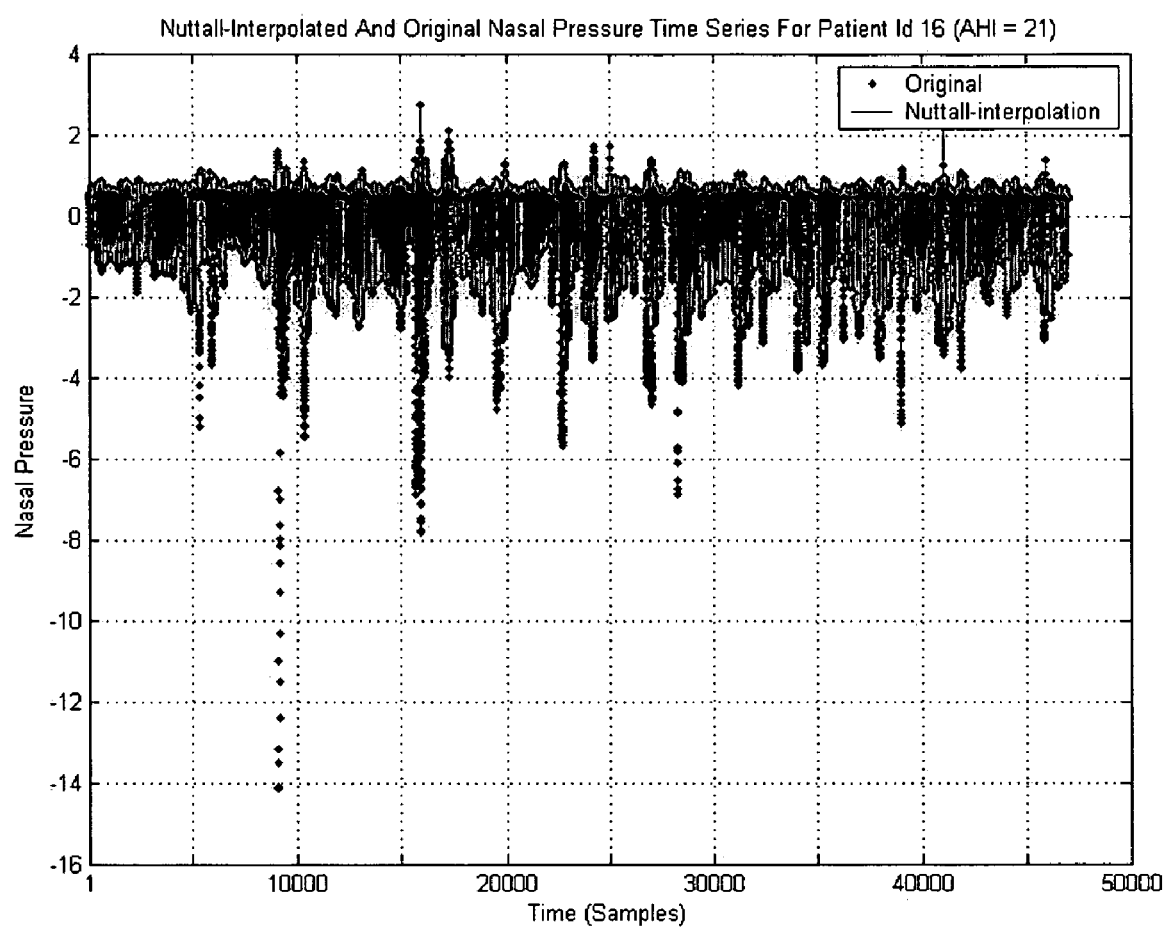
FIG. 2a is chart illustrating the removal of artifacts by the interpolation method.
Figure 2B:
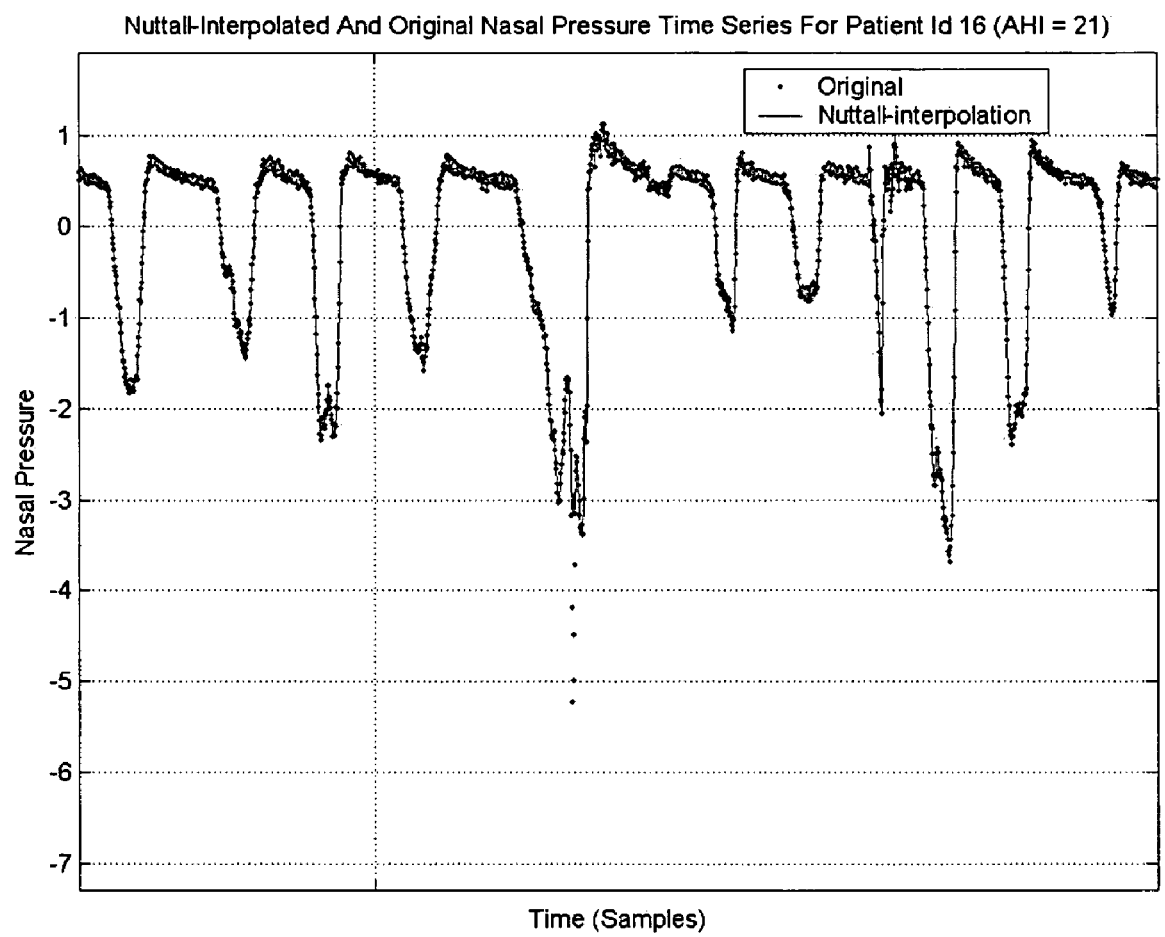

FIG. 2a provides a representation of how the interpolation routine patches the data by replacing points that cross above or below the threshold by linearly interpolated points obtained from points within the threshold. FIG. 2b provides an expanded view of a data segment from FIG. 2a.

Phase-Space Dynamical Reconstruction

From the scalar time series of the raw or interpolated physiologic measurement (e.g., nasal pressure), the phase-space dynamics may be reconstructed in higher dimensions according to the following paradigm. A d-dimensional set of vectors is obtained from a scalar time sequence of integer delays of the scalar observations:

$$y(n)=[v(n), v(n+T), v(n+2T), \ldots v(n+(d-1)T)]$$

where: v(n) is the original time series datum at time n; v(n+T) is datum from the same time series offset in the positive direction (or negative, e.g., v(n−T)) by time delay interval T; v(n+2T) is datum from the same time series offset in the positive direction by time delay interval 2T; v(n+(d−1)T) is the datum offset by time delay interval (d−1)T, and d is the embedding dimension; n is the index for the time series datum (n=1, 2, 3, . . . N); and the number of indices, N, may be as large as desired.

In performing the phase-space embedding, the initial task is to determine values for T and d. Moreover, one must ensure the time series has been sampled at a sufficiently high rate such that the time between sample points is shorter than the shortest time scale of physiologic relevance. The selection of the most suitable sample rate and number of data points are dependent on the physiologic time scales under consideration.

The geometric basis for underlying phase-space reconstruction is that, starting with a scalar time series of a single variable (i.e., in one dimension), one is able to reconstruct in m dimensions, the structure of a dynamical system in a so-called multivariate state-space in which the structure can be observed and quantified for further data processing. Generally, people observe in three dimensions, and higher dimensional structures are necessarily projected onto a three-dimensional (and sometimes two-dimensional) state-space. Nonetheless, computers may be used to compute high mathematical precision as many dimensions as the computer will reasonably allow.

When viewing three dimensional "chaotic attractors" with definite structure and pattern, oftentimes what is seen is a distortion that has been projected down onto the three-dimensional observation space. Even with the distortion, there frequently remains observable underlying structure, and it is a remarkable fact that systems, whose computed embedding dimensions are double and triple the observation space in which their orbits are viewed, show observable features which distinguish them apart.

Selection of Delay Parameter, T

To obtain an optimal choice for the delay parameter, T, the entropy of the signal in question must be determined. Nonlinear systems in a parameter regime where orbits are chaotic are known to generate entropy. Average mutual information (AMI) quantifies the information theoretic properties of the signal of interest. It answers the question: if data is collected in the form of a time series, v(n), perhaps from nasal pressure recordings where v(n)=v(t+n dt) and t is the start time, dt is the time between samples, and n is the sample number, how much information in bits, is obtained about the voltage level at time T later: namely, v(n dt+(T−t)).

The information theoretic answer to this question requires the distribution of measurements of these two quantities. The first of these distributions is P(v(n)), the second is P(v(n+T)), and the third is P(v(n),v(n+T)). The mutual information (MI) between these measurements is:

$$ln[P(v(n), v(n+T))/(P(v(n))P(v(n+T)))]$$

where the term in the numerator is the joint probability density between two measurable temporal events, the terms in the denominator are the individual probability densities for the two measurements, and MI is the natural logarithm of this ratio. For N observations, the average overall measurement is the AMI, which is a function of the delay parameter, T. Letting AMI=I(T), one obtains:

$$I(T)=I(T1)+I(T2)+ \ldots I(TN)$$

where: I(Tn)=P(v(n),v(n+T)) [ln (P(v(n),v(n+T))/(P(v(n)) P(v(n+T)))] and n=1,2, . . . N.

Note that for independent measurements v(n) and v(n+T), each term in the above sum vanishes due to the factorization of the joint probability P(a,b)=P(a)P(b). One would naturally expect two measurements to become independent for very large T since chaotic signals rapidly lose memory of earlier entries on their orbits. For the case T=0, I(0) is large, indicative of full knowledge of the measurements. In the general case, I(T)>0, one seeks an intermediate value where I(T) is neither too large or too small. Finding such a value for T will determine essentially independent measurements v(n) and v(n+T) in a nonlinear sense.

The nonlinear prescription for choosing such a value of T begins with the selection of the first minimum of I(T). This is done in the same spirit of choosing the first zero crossing of an autocorrelation function, often used in linear analysis. In practice, any value of T near the first minimum should suffice. However, a second condition is invoked, which is to err from the first minimum in the direction of decreasing T. This is done for two reasons. Firstly, as the AMI is based on a bivariate computation, and as the KAHUNA hypercube is selected as a (minimum) trivariate construct in one practical implementation, one must adjust the delay parameter appropriately as the dimension is increased.

For example, consider the bivariate case where T is prescribed as 30 sample units (i.e., T=30). For this case, the nonlinear dynamics of the signal will unfold rather nicely in a two-dimensional phase-space; however if attempting to reconstruct the dynamics in a three-dimensional phase-space, there is nothing precluding the dynamics from decorrelating in a nonlinear sense at a faster rate than T=30 would suggest. Suppose T is chosen to be less than 30, say by a factor of 0.5; ergo, T=15 now becomes a more appropriate choice of the delay parameter.

A second reason for reducing the value of the delay parameter has to do with evaluating patient data over a wide range of physiological conditions from normal to very sick. Since all patient data should be processed with the same input parameter settings leading into the detection device, there is no penalty paid in the physics of the measurement by shortening the delay parameter. This would not always be the case if the delay parameter was made longer.

Based on the above considerations and from the 16 patient data set described later, a delay of T=15 was determined to be optimal for the construction of a 3-dimensional phase-space geometry from which the differential radius and KAHUNA hyper-cube are subsequently derived. This value of 15 sample units is based on a data pool of perfectly normal (AHI=0) to very sick (AHI=35) patients in which the corresponding first minima of the AMI ranged from approximately T=40 for the healthy individuals to about T=3 for the very sick individuals. The specific physiological time series used for these assessments of the delay parameter were nasal pressure daytime recordings of record lengths of approximately 15–20 minutes in which a digital sample record was obtained for computer manipulation based on a sampling rate of 40 samples per second (i.e., 40 Hz). A typical record length ranged from 36000 to 48000 sample points.

Selection of Embedding Dimension

The technique employed for computing the minimum embedding dimension is based on the idea that when points of higher dimension are projected down to a space of lower dimension, there are overlapping orbits in the low dimension space, such that if the process was reversed and the projected space unfolded to a higher dimension, neighboring points along the trajectory would be expected to separate. Hence, the technique starting with dimension one unfolds to higher and higher dimensions, while keeping track of the percentage of nearest neighbors that spread apart at each integer increase of dimension. Enough additional coordinates have been added when all points are near each other for dynamical reasons, rather than by projection from a higher dimension.

Next is determining in dimension "d" which points, made out of the time delays into vectors as above, are the nearest neighbors ynn(n) of the point y(n), where ynn(n) is computed in the usual way as:

$$ynn(n)=[vnn(n),vnn(n+T),\ldots vnn(n+(d-1)T)]$$

It is determined whether or not these points remain near in dimension (d+1), where the vector y(n) is augmented by a component v(n+dT) and ynn(n) is augmented by vnn(n+dT). For small distances, the neighbors are true neighbors. For large distances, there are false neighbors that arrived near each other through projection. When the percentage of false neighbors drops to zero, the attractor has been unfolded onto a practical dimensional space defined by the minimum embedding dimension. The space is practical in the sense that the dynamical reconstruction of the signal of interest is optimized while minimizing computer processing by avoiding unnecessary over-embedding. For the sixteen patient data set from the clinical trial (described below), typical embedding dimensions ranged between 4 and 6.

It is not always necessary to model or process data in the exact dimension of the system. Frequently, lower projections are used which can provide equally useful results. For data processing of cardio-respiratory physiological variables, three-dimensional embeddings worked successfully for our purposes. Reduction of the dimension whenever feasible has the advantage of reducing computational load (as seen in the present case) by as much as four orders of magnitude or better.

Chaotic and Differential Radius

Once the most appropriate phase-space reconstruction parameters are established, the digital time record of physiological measurements can be applied to generate the phase-space orbits or trajectories. One useful tool for quantifying erratic deflections of the fiducial orbit, where "fiducial orbit" is defined as the principal orbit on which points in phase-space evolve, is to construct the differential radius (DR) of orbital points. Since the DR derives from a similar useful metric which is called the chaotic radius (CR), the CR is first described. (The chaotic radius is so named as a matter of convenience and is not always intended to imply 'chaos' in the strict mathematical sense.)

The CR is defined as the Euclidean distance in N dimensions from a reference point in phase-space (e.g., usually, taken as the origin) to any given point in the phase-space orbit. Consider for illustration the two-dimensional case. Let X(n) be the measured digital signal and first component sequence of the two-dimensional orbital sequence, and let X(n+T) be the second component of the same sequence, where n=1,2 . . . N. Then the chaotic radius is defined by:

$$CR=\sqrt{X(n)^2+X(n+T)^2}$$

The DR is the temporal derivative of the CR. The DR is a quantification metric that determines irregularity on a phase-space orbit by marking how points change or deflect from one state to the next. It is not intended to say anything about the invariance of system dynamics or processes, nor does it necessarily imply chaos. Rather, it can be applied to any time series and is used to complement other techniques and certain classes of models (e.g., nonlinear differential equations, stochastic models) or data measurement procedures, to provide enhanced discriminability.

From the above computation of CR, let the points X(n) and X(n+T) represent, as before, the component magnitudes of a two-dimensional vector at time n, and now also let points X(n+d) and X(n+T+d) respectively represent the change in magnitude between two successive points at n and n+d. Consequently the DR can be determined from:

$$DR=\sqrt{[X(n+d)-X(n)]^2+[X(n+d+T)-X(n+T)]^2}$$

Figure 3:
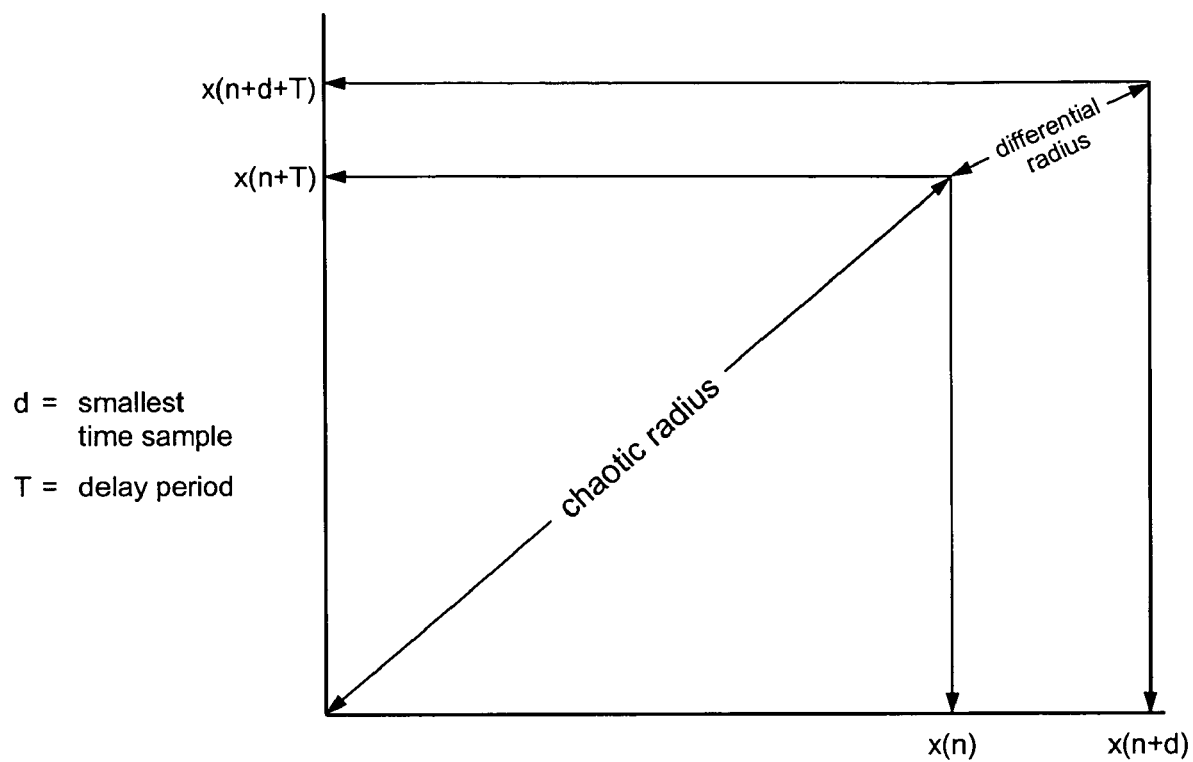
FIG. 3 is a graph showing the computation of chaotic and differential radii.

FIG. 3 provides a geometrical interpretation of CR and DR for the two-dimensional case. As noted earlier, the DR is a discriminant of irregularity in a time series. It is particularly well-suited to time series patterns that are known to have some degree of regularity or oscillatory behavior. This is known to be generally the case for a number of well known physiologic signals such at heart beat (e.g., average 72 beats per minute) or breathing cycle (e.g., average 15 breaths per minute) among others. However, instead of measuring the regularity of the signal of interest, the DR measures the deflection or departure from the most regular physiological state under normal conditions. Therefore, a large number of deflections of significant magnitude (i.e., magnitude in the sense of Euclidean distance in phase-space) arising from a physiologic time trace, are indicative of a pathological condition.

Figure 4:
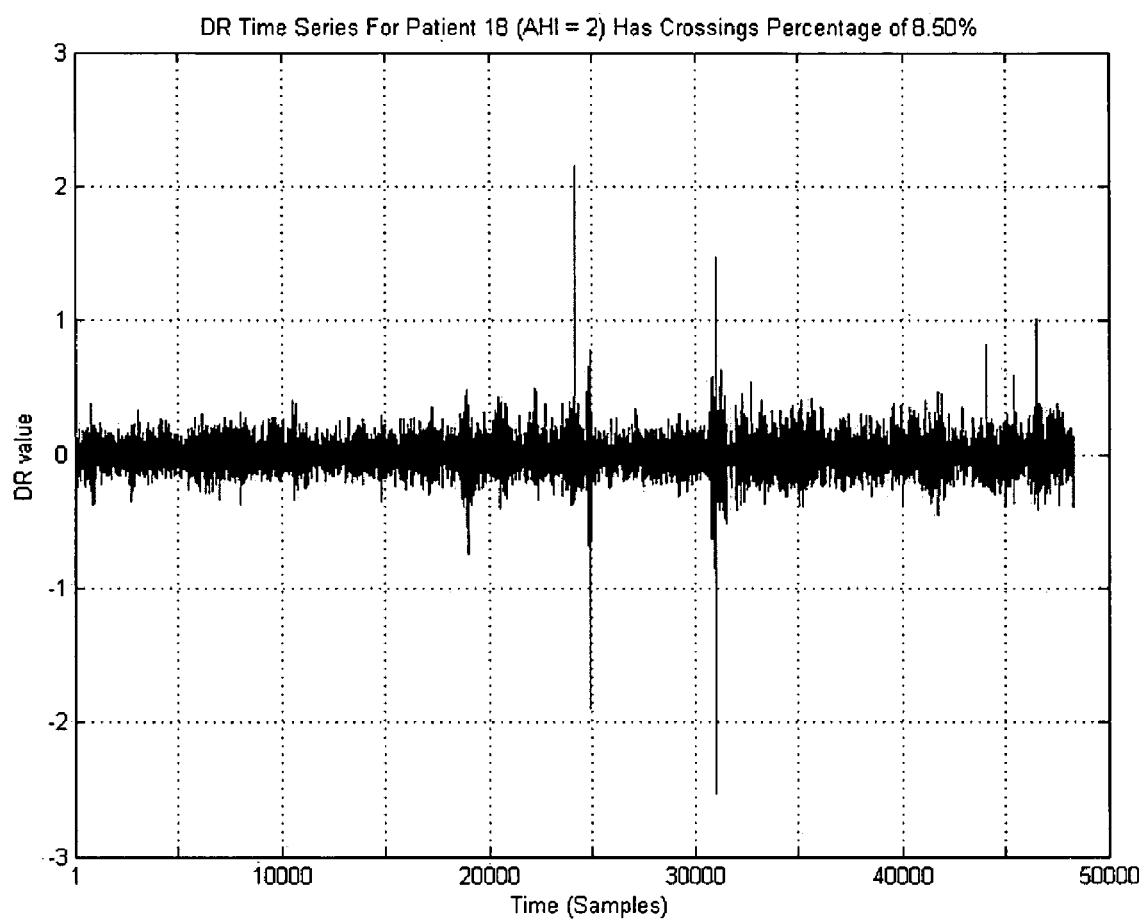
FIG. 4 is a chart illustrating differential radii obtained from a normal patient.
Figure 5:
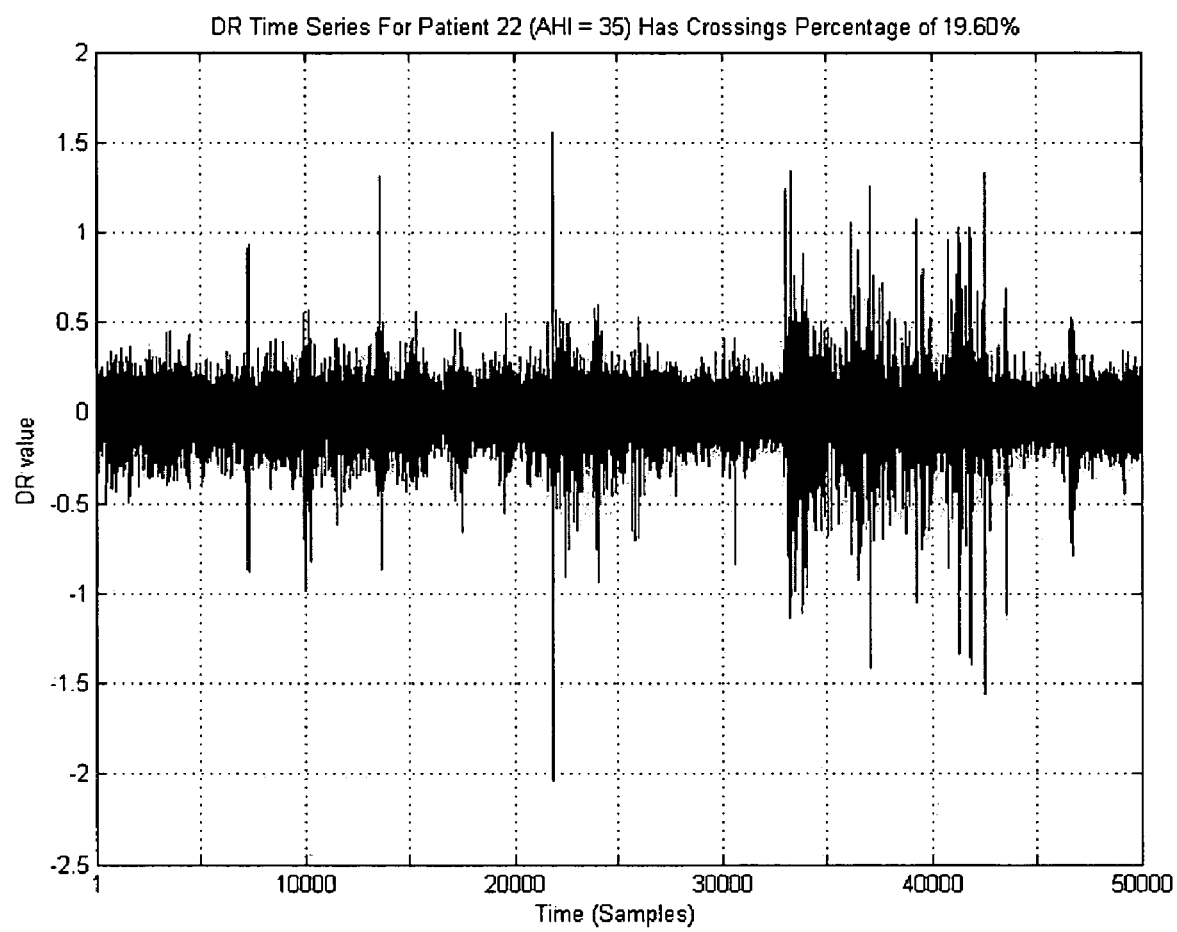
FIG. 5 is a graph showing differential radii obtained from a sick patient.

As examples, FIGS. 4 and 5 respectively show DR plots for two human subjects, one normal and the other afflicted with a severe apnea. Notice the DR trace for the apnea-afflicted subject has a much larger variation than that of the normal subject. In fact, for a threshold crossing level set at plus-or-minus 0.15, there are more than double the number of crossings of the threshold, about 20% of the total sample points for the apnea patient (AHI=35) than are indicated for the normal patient (AHI=2) where the percentage of crossings is just under 9%. Therefore, based on these and other similar cases, the DR can be an excellent clinical marker for discriminating between sick and healthy patients.

KAHUNA Hypercube

The KAHUNA hypercube is a mathematical construction that covers phase-space with a large number of n-dimensional non-overlapping cubes of equal proportion. The total number of mini-cubes comprising the larger KAHUNA cube can be as large as is desirable, within the practical limits of the computer. In an exemplary embodiment described in three dimensions, KAHUNA cubes were evaluated ranging from a total of 512 mini-cubes (i.e., size 8×8×8) to 9261 mini-cubes (i.e., size 21×21×21).

The KAHUNA cube serves three major purposes for the quantification of the dynamics in phase-space. First, it can identify the highest density region of the phase-space that orbiting points pass through. Secondly, it can quantify the dispersive characteristics of the attractor, and thirdly, it can quantify the shape of the attractor. These quantitative attributes were found to be quite useful for delineating healthy versus unhealthy subjects in the 16-patient blind trial described below.

Tables 1–3 respectively show KAHUNA computed results for three separate (baseline) criterion for defining disease, in which subjects with AHI scores >=5, >=6, and >=13 are deemed to be apnea-afflicted. The first two columns in each table provide the threshold criterion upon which the health state of the subject is determined. The first column of numbers gives values for the minimum acceptable ratio as a percentage of points that pass through a given mini-cube, divided by the maximum number of points that pass through the mini-cube of the maximum density. The second column of numbers indicates the minimum number of mini-cubes required for which the column one criterion also applies. Together, the two columns of numbers define the thresholds for quantifying the dispersive nature of the attractor, where the working hypothesis states: Low dispersion of points on the attractor implies a tendency towards sickness and a high dispersion tends to normalcy.

The next six columns in the table provide performance results. Column number 3 gives the number of subjects in the test actually afflicted by the disease according to the prescribed AHI criterion. Column number 4 indicates how many subjects with the disease the KAHUNA algorithm correctly classified. Column number 5 provides the number of false negatives called by the algorithm, where a false negative defines the situation wherein the subject is deemed to be sick, but the algorithm does not detect the sickness. Column number 6 delineates subjects from the group who are deemed to be normal according to the AHI criterion. Column number 7 gives the number of correct dismissals called by the algorithm, and column number 8 gives the number of false positives called by the algorithm; namely, false positives are those cases where the subject is deemed to be healthy according to the prescribed AHI criterion, and the algorithm incorrectly determines the subject to be unhealthy. Finally, the last column gives the success rate of the KAHUNA method based upon the specified criteria. It should be noted that the threshold criteria for quantifying dispersion characteristics (columns numbers 1 and 2) of the attractor, are determined from the data themselves within the computer model, and are not subjectively determined.

For the case where AHI>=5 defines sickness (see Table 1), the algorithm performed correctly 100% of the time; namely, of the thirteen patients tested by the KAHUNA algorithm, 13 were correctly classified, in which 11 were deemed to be sick and the other two were deemed to be normal. There were three additional subjects that were from the original group of sixteen subjects tested by the preceding DR test that correctly classified three sick patients (see FIG. 1). Therefore, the total success rate remains at 100% for 16 of 16 subjects correctly classified based upon the defining criterion. Tables 2 and 3 show a success rate of about 85% if the prescribed normalcy criterion is relaxed from an AHI of 4 or less to an AHI of 5 or less and to an AHI of 12 or less, respectively. Adding in the 3 successes from the DR test boosts the tally (for the total 16 subjects) to a success rate of 88%.

Figure 6:
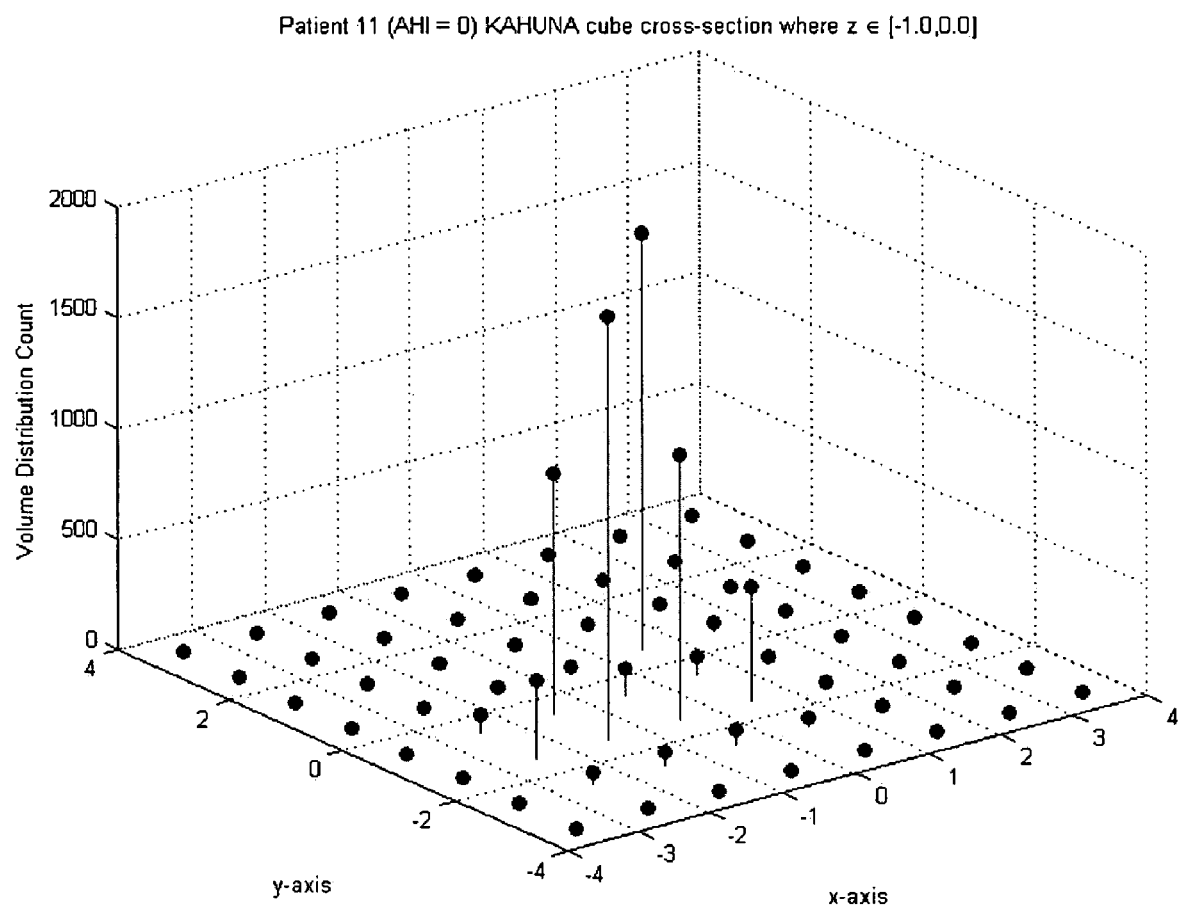
FIG. 6 is a chart illustrating a KAHUNA cube of a normal patient.
Figure 7:
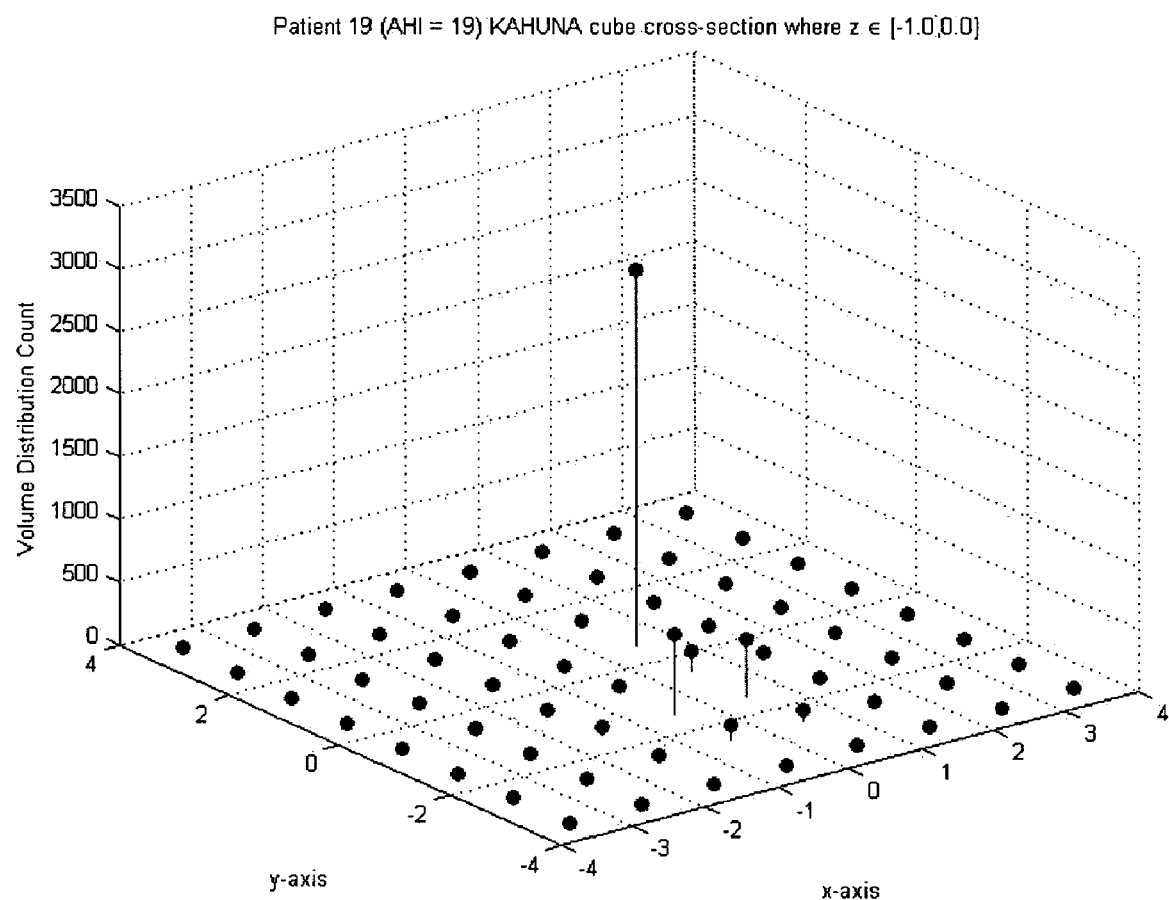
FIG. 7 is a graph showing a KAHUNA cube of a sick patient.
Figure 8:
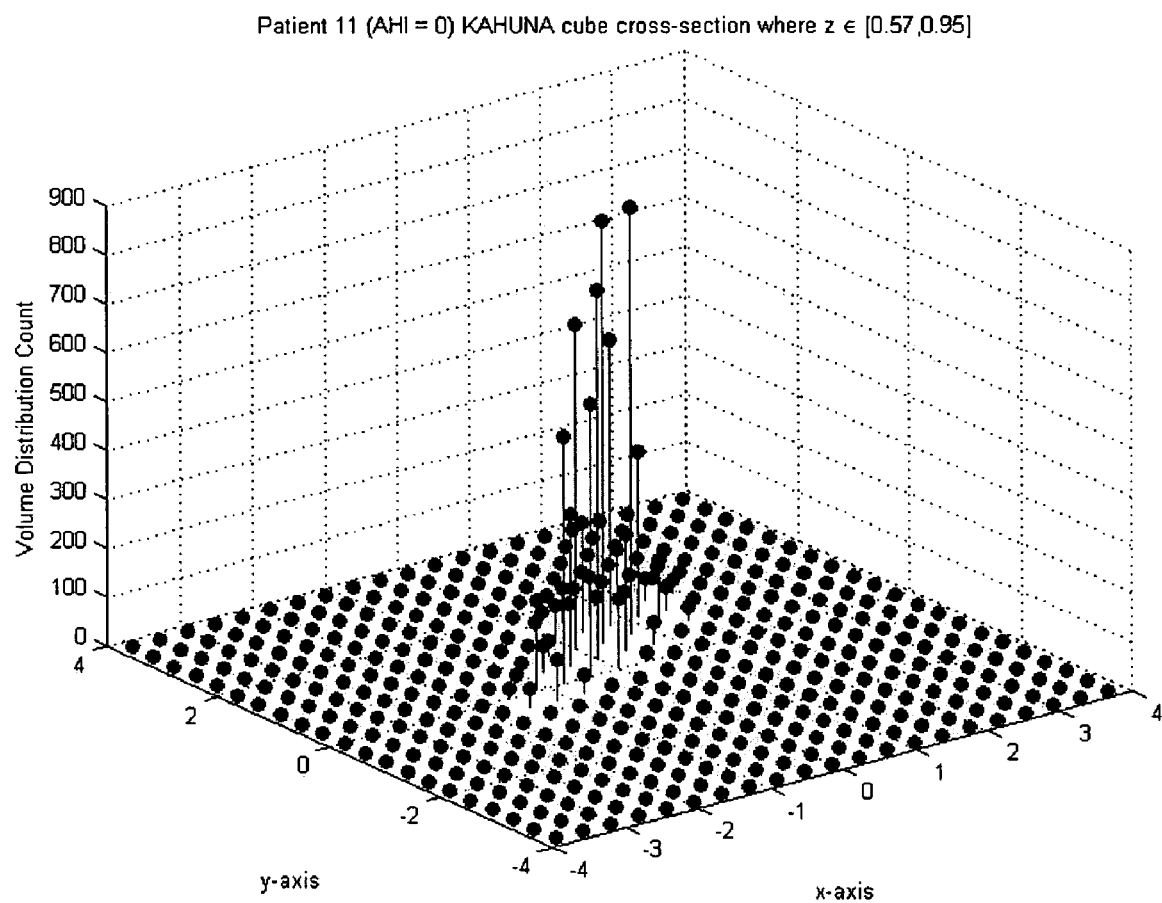
FIG. 8 is a chart illustrating the high fidelity midsection of a KAHUNA cube of a normal patient.

Illustrating the KAHUNA hypercube at work, FIGS. 6 and 7 respectively show density plots of a perpendicular slice through the midsection of the vertical-plane for a patient deemed to be normal (AHI=0) and for a patient with apnea (AHI=19). The volume distribution count (i.e., the number of points landing in a given mini-cube) for this slice of this 8×8×8 three-dimensional cube is indicated on the vertical scale. Note the low dispersive quality of points for the sick patient in contrast to the high dispersive quality for the normal patient. Finally, FIG. 8 shows a representative slice from a density plot for a high fidelity three-dimensional cube in dimension 21×21×21. This latter depiction of the KAHUNA is useful for exploring the fine detail of clustering and the shape of the attractor for template-matching subjects in stratified groupings. Note that the KAHUNA can also be computed in N dimensions where N>3, and also note that the value of m representing number of divisions of the hypercube (i.e., $m_1 \times m_2 \times \ldots m_N$) can be adjusted appropriately to ascertain an optimal measure for the density of orbits.

Clinical Trial Results

In order to describe the operation and utility of the present invention, the method is demonstrated to physiologic recordings from a blind trial of 16 patients in which data were collected at a major hospital (in Providence, R.I.) and in which the patients were also subjected to a full nighttime conventional (8–10 hour) polysomography in which Apnea Hypopnea Index (AHI) scores were made available only to the hospital physicians and clinicians. On a separate occasion, the same patients were re-tested during the daytime in a short time interval (20 minutes) using our nonlinear signal processing phase-space method that combines the Differential Radius and KAHUNA hypercube technique. For the daytime test, the patient condition (degree of apnea) was not revealed to the examiners of the nonlinear method. Examiners for the daytime test (blind trial) viewed 7 color-coded regions in three dimensions, and furthermore by application of the KAHUNA hypercube, examiners were able to view in fine detail from 512 up to 9261 (or greater) distinct spatial regions of orbiting points in phase-space.

The results of the trial showed that for patients whose baseline polysomography scores were in the range of AHI indices of 5 and above, where an index of 5 or greater defines the presence of a sleep disorder (i.e., apnea), the automatic detection device was successful 100% of the time (i.e., 16 of 16 correct classifications of patients in which there were only 3 normals in the group where patients had associated AHI indices less than 5). Moreover, for AHI scoring of the same patient group, where AHI indices of 6 and above define sleep apnea, the automatic detection device classified correctly 87.5% of the time (14 out of 16). Finally, from the same patient group where an AHI index above 12 defines an apnea, the automatic detection device scored equally as well (87.5%). For an AHI index of less than 5, considered as the normal range, there were no false negative and no false positive classifications. For the case considered where AHI indices of 6 and above define an apnea, there was 1 false negative and 1 false positive misclassification of the automatic detection device. For the case considered where AHI indices of 13 and above denote an apnea, there also was 1 false negative and 1 false positive misclassification.

Note that the scoring of the AHI and diagnosis of the patient's respiratory condition from nighttime polysomnography measurements alone remains an imprecise science, and different demarcations of the AHI index denoting a patient who is apnea afflicted (e.g., AHI index greater than 4, greater than 5, or greater than 12, as examples) remains a subjective call on the part of the attending physician or clinician. On the other hand, the method of the present invention is fully automated and computerized, and is completely defined in quantifiable terms in which human subjectivity is removed from the scoring process. A unique feature of the method is that various thresholds invoked during the data processing are determined from the data itself, rather than by arbitrarily imposing thresholds, as is often the case for a large variety of signal detection algorithms.

TABLE 1

Dispersion Test Parameters Yielding Optimal Performance for 13-Patient Data Set Where Apnea-Hypopnea Index (AHI) >= 5 Indicates Sickness

| Sub-Threshold Criteria % | # cubes | Apnea Pats. | Detects | False Neg. | Normal Pats. | Correct Dismiss. | False Pos. | Success Rate |
|---|---|---|---|---|---|---|---|---|
| 4.2 | 13 | 11 | 11 | 0 | 2 | 2 | 0 | 100.00% |
| 4.3 | 13 | 11 | 11 | 0 | 2 | 2 | 0 | 100.00% |
| 4.4 | 13 | 11 | 11 | 0 | 2 | 2 | 0 | 100.00% |
| 4.5 | 13 | 11 | 11 | 0 | 2 | 2 | 0 | 100.00% |
| 4.6 | 12 | 11 | 11 | 0 | 2 | 2 | 0 | 100.00% |
| 4.6 | 13 | 11 | 11 | 0 | 2 | 2 | 0 | 100.00% |
| 4.7 | 12 | 11 | 11 | 0 | 2 | 2 | 0 | 100.00% |
| 4.7 | 13 | 11 | 11 | 0 | 2 | 2 | 0 | 100.00% |
| 4.8 | 12 | 11 | 11 | 0 | 2 | 2 | 0 | 100.00% |
| 4.8 | 13 | 11 | 11 | 0 | 2 | 2 | 0 | 100.00% |
| 4.9 | 12 | 11 | 11 | 0 | 2 | 2 | 0 | 100.00% |
| 4.9 | 13 | 11 | 11 | 0 | 2 | 2 | 0 | 100.00% |
| 5.0 | 12 | 11 | 11 | 0 | 2 | 2 | 0 | 100.00% |
| 5.0 | 13 | 11 | 11 | 0 | 2 | 2 | 0 | 100.00% |
| 5.1 | 12 | 11 | 11 | 0 | 2 | 2 | 0 | 100.00% |
| 5.1 | 13 | 11 | 11 | 0 | 2 | 2 | 0 | 100.00% |
| 5.2 | 12 | 11 | 11 | 0 | 2 | 2 | 0 | 100.00% |
| 5.2 | 13 | 11 | 11 | 0 | 2 | 2 | 0 | 100.00% |
| 5.3 | 12 | 11 | 11 | 0 | 2 | 2 | 0 | 100.00% |
| 5.3 | 13 | 11 | 11 | 0 | 2 | 2 | 0 | 100.00% |
| 5.4 | 11 | 11 | 11 | 0 | 2 | 2 | 0 | 100.00% |
| 5.4 | 12 | 11 | 11 | 0 | 2 | 2 | 0 | 100.00% |
| 5.4 | 13 | 11 | 11 | 0 | 2 | 2 | 0 | 100.00% |
| 5.5 | 11 | 11 | 11 | 0 | 2 | 2 | 0 | 100.00% |
| 5.5 | 12 | 11 | 11 | 0 | 2 | 2 | 0 | 100.00% |
| 5.5 | 13 | 11 | 11 | 0 | 2 | 2 | 0 | 100.00% |
| 5.6 | 11 | 11 | 11 | 0 | 2 | 2 | 0 | 100.00% |
| 5.6 | 12 | 11 | 11 | 0 | 2 | 2 | 0 | 100.00% |
| 5.6 | 13 | 11 | 11 | 0 | 2 | 2 | 0 | 100.00% |
| 5.7 | 10 | 11 | 11 | 0 | 2 | 2 | 0 | 100.00% |
| 5.7 | 11 | 11 | 11 | 0 | 2 | 2 | 0 | 100.00% |
| 5.7 | 12 | 11 | 11 | 0 | 2 | 2 | 0 | 100.00% |
| 5.7 | 13 | 11 | 11 | 0 | 2 | 2 | 0 | 100.00% |
| 5.8 | 10 | 11 | 11 | 0 | 2 | 2 | 0 | 100.00% |
| 5.8 | 11 | 11 | 11 | 0 | 2 | 2 | 0 | 100.00% |
| 5.8 | 12 | 11 | 11 | 0 | 2 | 2 | 0 | 100.00% |
| 5.8 | 13 | 11 | 11 | 0 | 2 | 2 | 0 | 100.00% |
| 5.9 | 10 | 11 | 11 | 0 | 2 | 2 | 0 | 100.00% |
| 5.9 | 11 | 11 | 11 | 0 | 2 | 2 | 0 | 100.00% |
| 5.9 | 12 | 11 | 11 | 0 | 2 | 2 | 0 | 100.00% |
| 5.9 | 9 | 11 | 11 | 0 | 2 | 2 | 0 | 100.00% |
| 6.0 | 10 | 11 | 11 | 0 | 2 | 2 | 0 | 100.00% |
| 6.0 | 11 | 11 | 11 | 0 | 2 | 2 | 0 | 100.00% |
| 6.0 | 12 | 11 | 11 | 0 | 2 | 2 | 0 | 100.00% |
| 6.0 | 9 | 11 | 11 | 0 | 2 | 2 | 0 | 100.00% |
| 6.1 | 10 | 11 | 11 | 0 | 2 | 2 | 0 | 100.00% |
| 6.1 | 11 | 11 | 11 | 0 | 2 | 2 | 0 | 100.00% |
| 6.1 | 12 | 11 | 11 | 0 | 2 | 2 | 0 | 100.00% |
| 6.1 | 9 | 11 | 11 | 0 | 2 | 2 | 0 | 100.00% |
| 6.2 | 10 | 11 | 11 | 0 | 2 | 2 | 0 | 100.00% |
| 6.2 | 11 | 11 | 11 | 0 | 2 | 2 | 0 | 100.00% |
| 6.2 | 12 | 11 | 11 | 0 | 2 | 2 | 0 | 100.00% |
| 6.2 | 9 | 11 | 11 | 0 | 2 | 2 | 0 | 100.00% |
| 6.3 | 10 | 11 | 11 | 0 | 2 | 2 | 0 | 100.00% |
| 6.3 | 11 | 11 | 11 | 0 | 2 | 2 | 0 | 100.00% |
| 6.3 | 9 | 11 | 11 | 0 | 2 | 2 | 0 | 100.00% |
| 6.4 | 10 | 11 | 11 | 0 | 2 | 2 | 0 | 100.00% |
| 6.4 | 11 | 11 | 11 | 0 | 2 | 2 | 0 | 100.00% |
| 6.4 | 9 | 11 | 11 | 0 | 2 | 2 | 0 | 100.00% |
| 6.5 | 10 | 11 | 11 | 0 | 2 | 2 | 0 | 100.00% |
| 6.5 | 11 | 11 | 11 | 0 | 2 | 2 | 0 | 100.00% |
| 6.5 | 8 | 11 | 11 | 0 | 2 | 2 | 0 | 100.00% |
| 6.5 | 9 | 11 | 11 | 0 | 2 | 2 | 0 | 100.00% |
| 6.6 | 10 | 11 | 11 | 0 | 2 | 2 | 0 | 100.00% |
| 6.6 | 11 | 11 | 11 | 0 | 2 | 2 | 0 | 100.00% |
| 6.6 | 8 | 11 | 11 | 0 | 2 | 2 | 0 | 100.00% |
| 6.6 | 9 | 11 | 11 | 0 | 2 | 2 | 0 | 100.00% |
| 6.7 | 10 | 11 | 11 | 0 | 2 | 2 | 0 | 100.00% |
| 6.7 | 7 | 11 | 11 | 0 | 2 | 2 | 0 | 100.00% |
| 6.7 | 8 | 11 | 11 | 0 | 2 | 2 | 0 | 100.00% |
| 6.7 | 9 | 11 | 11 | 0 | 2 | 2 | 0 | 100.00% |
| 6.8 | 10 | 11 | 11 | 0 | 2 | 2 | 0 | 100.00% |
| 6.8 | 7 | 11 | 11 | 0 | 2 | 2 | 0 | 100.00% |
| 6.8 | 8 | 11 | 11 | 0 | 2 | 2 | 0 | 100.00% |
| 6.8 | 9 | 11 | 11 | 0 | 2 | 2 | 0 | 100.00% |
| 6.9 | 10 | 11 | 11 | 0 | 2 | 2 | 0 | 100.00% |
| 6.9 | 7 | 11 | 11 | 0 | 2 | 2 | 0 | 100.00% |
| 6.9 | 8 | 11 | 11 | 0 | 2 | 2 | 0 | 100.00% |
| 6.9 | 9 | 11 | 11 | 0 | 2 | 2 | 0 | 100.00% |
| 7.0 | 7 | 11 | 11 | 0 | 2 | 2 | 0 | 100.00% |
| 7.0 | 8 | 11 | 11 | 0 | 2 | 2 | 0 | 100.00% |
| 7.1 | 7 | 11 | 11 | 0 | 2 | 2 | 0 | 100.00% |
| 7.1 | 8 | 11 | 11 | 0 | 2 | 2 | 0 | 100.00% |
| 7.1 | 9 | 11 | 11 | 0 | 2 | 2 | 0 | 100.00% |
| 7.2 | 7 | 11 | 11 | 0 | 2 | 2 | 0 | 100.00% |
| 7.2 | 8 | 11 | 11 | 0 | 2 | 2 | 0 | 100.00% |
| 7.3 | 7 | 11 | 11 | 0 | 2 | 2 | 0 | 100.00% |
| 7.3 | 8 | 11 | 11 | 0 | 2 | 2 | 0 | 100.00% |
| 7.4 | 7 | 11 | 11 | 0 | 2 | 2 | 0 | 100.00% |
| 7.4 | 8 | 11 | 11 | 0 | 2 | 2 | 0 | 100.00% |
| 7.5 | 7 | 11 | 11 | 0 | 2 | 2 | 0 | 100.00% |
| 7.5 | 8 | 11 | 11 | 0 | 2 | 2 | 0 | 100.00% |
| 7.6 | 7 | 11 | 11 | 0 | 2 | 2 | 0 | 100.00% |
| 7.6 | 8 | 11 | 11 | 0 | 2 | 2 | 0 | 100.00% |
| 7.7 | 7 | 11 | 11 | 0 | 2 | 2 | 0 | 100.00% |
| 7.7 | 8 | 11 | 11 | 0 | 2 | 2 | 0 | 100.00% |
| 7.8 | 7 | 11 | 11 | 0 | 2 | 2 | 0 | 100.00% |
| 7.8 | 8 | 11 | 11 | 0 | 2 | 2 | 0 | 100.00% |
| 7.9 | 6 | 11 | 11 | 0 | 2 | 2 | 0 | 100.00% |
| 7.9 | 7 | 11 | 11 | 0 | 2 | 2 | 0 | 100.00% |
| 7.9 | 8 | 11 | 11 | 0 | 2 | 2 | 0 | 100.00% |
| 8.0 | 6 | 11 | 11 | 0 | 2 | 2 | 0 | 100.00% |
| 8.0 | 7 | 11 | 11 | 0 | 2 | 2 | 0 | 100.00% |
| 8.0 | 8 | 11 | 11 | 0 | 2 | 2 | 0 | 100.00% |
| 8.1 | 6 | 11 | 11 | 0 | 2 | 2 | 0 | 100.00% |
| 8.1 | 7 | 11 | 11 | 0 | 2 | 2 | 0 | 100.00% |
| 8.2 | 6 | 11 | 11 | 0 | 2 | 2 | 0 | 100.00% |
| 8.2 | 7 | 11 | 11 | 0 | 2 | 2 | 0 | 100.00% |

TABLE 1-continued

Dispersion Test Parameters Yielding Optimal Performance for 13-Patient Data Set Where Apnea-Hypopnea Index (AHI) >= 5 Indicates Sickness

| Sub-Threshold Criteria | | | | | | | | |
|---|---|---|---|---|---|---|---|---|
| % | # cubes | Apnea Pats. | De-tects | False Neg. | Normal Pats. | Dis-miss. | False Pos. | Success Rate |
| 8.3 | 6 | 11 | 11 | 0 | 2 | 2 | 0 | 100.00% |
| 8.3 | 7 | 11 | 11 | 0 | 2 | 2 | 0 | 100.00% |
| 8.4 | 6 | 11 | 11 | 0 | 2 | 2 | 0 | 100.00% |
| 8.4 | 7 | 11 | 11 | 0 | 2 | 2 | 0 | 100.00% |
| 8.5 | 6 | 11 | 11 | 0 | 2 | 2 | 0 | 100.00% |
| 8.5 | 7 | 11 | 11 | 0 | 2 | 2 | 0 | 100.00% |
| 8.6 | 6 | 11 | 11 | 0 | 2 | 2 | 0 | 100.00% |
| 8.6 | 7 | 11 | 11 | 0 | 2 | 2 | 0 | 100.00% |
| 8.7 | 6 | 11 | 11 | 0 | 2 | 2 | 0 | 100.00% |
| 8.7 | 7 | 11 | 11 | 0 | 2 | 2 | 0 | 100.00% |
| 8.8 | 6 | 11 | 11 | 0 | 2 | 2 | 0 | 100.00% |
| 8.8 | 7 | 11 | 11 | 0 | 2 | 2 | 0 | 100.00% |
| 8.9 | 6 | 11 | 11 | 0 | 2 | 2 | 0 | 100.00% |
| 9.0 | 5 | 11 | 11 | 0 | 2 | 2 | 0 | 100.00% |
| 9.0 | 6 | 11 | 11 | 0 | 2 | 2 | 0 | 100.00% |
| 9.1 | 5 | 11 | 11 | 0 | 2 | 2 | 0 | 100.00% |
| 9.1 | 6 | 11 | 11 | 0 | 2 | 2 | 0 | 100.00% |
| 9.2 | 5 | 11 | 11 | 0 | 2 | 2 | 0 | 100.00% |
| 9.2 | 6 | 11 | 11 | 0 | 2 | 2 | 0 | 100.00% |
| 9.3 | 5 | 11 | 11 | 0 | 2 | 2 | 0 | 100.00% |
| 9.3 | 6 | 11 | 11 | 0 | 2 | 2 | 0 | 100.00% |
| 9.4 | 5 | 11 | 11 | 0 | 2 | 2 | 0 | 100.00% |
| 9.5 | 5 | 11 | 11 | 0 | 2 | 2 | 0 | 100.00% |
| 9.6 | 5 | 11 | 11 | 0 | 2 | 2 | 0 | 100.00% |
| 9.7 | 5 | 11 | 11 | 0 | 2 | 2 | 0 | 100.00% |
| 9.8 | 5 | 11 | 11 | 0 | 2 | 2 | 0 | 100.00% |
| 9.9 | 5 | 11 | 11 | 0 | 2 | 2 | 0 | 100.00% |
| 10.0 | 5 | 11 | 11 | 0 | 2 | 2 | 0 | 100.00% |
| 10.1 | 5 | 11 | 11 | 0 | 2 | 2 | 0 | 100.00% |
| 10.2 | 5 | 11 | 11 | 0 | 2 | 2 | 0 | 100.00% |
| 10.3 | 5 | 11 | 11 | 0 | 2 | 2 | 0 | 100.00% |
| 10.4 | 5 | 11 | 11 | 0 | 2 | 2 | 0 | 100.00% |
| 10.5 | 5 | 11 | 11 | 0 | 2 | 2 | 0 | 100.00% |

TABLE 2

Dispersion Test Parameters Yielding Optimal Performance for 13-Patient Data Set Where Apnea-Hypopnea Index (AHI) >= 6 Indicates Sickness

| Sub-Threshold Criteria | | | | | | | | |
|---|---|---|---|---|---|---|---|---|
| % | # cubes | Apnea Pats. | De-tects | False Neg. | Normal Pats. | Dis-miss. | False Pos. | Success Rate |
| 8.5 | 4 | 9 | 8 | 1 | 4 | 3 | 1 | 84.62% |
| 8.6 | 4 | 9 | 8 | 1 | 4 | 3 | 1 | 84.62% |
| 8.7 | 4 | 9 | 8 | 1 | 4 | 3 | 1 | 84.62% |
| 8.8 | 4 | 9 | 8 | 1 | 4 | 3 | 1 | 84.62% |
| 8.9 | 4 | 9 | 8 | 1 | 4 | 3 | 1 | 84.62% |
| 9.0 | 4 | 9 | 8 | 1 | 4 | 3 | 1 | 84.62% |
| 9.1 | 4 | 9 | 8 | 1 | 4 | 3 | 1 | 84.62% |
| 9.2 | 4 | 9 | 8 | 1 | 4 | 3 | 1 | 84.62% |
| 9.3 | 4 | 9 | 8 | 1 | 4 | 3 | 1 | 84.62% |
| 9.4 | 4 | 9 | 8 | 1 | 4 | 3 | 1 | 84.62% |
| 9.5 | 4 | 9 | 8 | 1 | 4 | 3 | 1 | 84.62% |
| 9.6 | 4 | 9 | 8 | 1 | 4 | 3 | 1 | 84.62% |
| 9.7 | 4 | 9 | 8 | 1 | 4 | 3 | 1 | 84.62% |
| 9.8 | 4 | 9 | 8 | 1 | 4 | 3 | 1 | 84.62% |
| 9.9 | 4 | 9 | 8 | 1 | 4 | 3 | 1 | 84.62% |
| 10.0 | 4 | 9 | 8 | 1 | 4 | 3 | 1 | 84.62% |
| 10.1 | 4 | 9 | 8 | 1 | 4 | 3 | 1 | 84.62% |
| 10.2 | 4 | 9 | 8 | 1 | 4 | 3 | 1 | 84.62% |

TABLE 2-continued

Dispersion Test Parameters Yielding Optimal Performance for 13-Patient Data Set Where Apnea-Hypopnea Index (AHI) >= 6 Indicates Sickness

| Sub-Threshold Criteria | | | | | | | | |
|---|---|---|---|---|---|---|---|---|
| % | # cubes | Apnea Pats. | De-tects | False Neg. | Normal Pats. | Dis-miss. | False Pos. | Success Rate |
| 10.3 | 4 | 9 | 8 | 1 | 4 | 3 | 1 | 84.62% |
| 10.4 | 4 | 9 | 8 | 1 | 4 | 3 | 1 | 84.62% |
| 10.5 | 4 | 9 | 8 | 1 | 4 | 3 | 1 | 84.62% |

TABLE 3

Dispersion Test Parameters Yielding Optimal Performance for 13-Patient Data Set Where Apnea-Hypopnea Index (AHI) >= 13 Indicates Sickness

| Sub-Threshold Criteria | | | | | | | | |
|---|---|---|---|---|---|---|---|---|
| % | # cubes | Apnea Pats. | De-tects | False Neg. | Normal Pats. | Dis-miss. | False Pos. | Success Rate |
| 9.3 | 1 | 4 | 3 | 1 | 9 | 8 | 1 | 84.62% |
| 9.4 | 1 | 4 | 3 | 1 | 9 | 8 | 1 | 84.62% |
| 9.5 | 1 | 4 | 3 | 1 | 9 | 8 | 1 | 84.62% |
| 9.6 | 1 | 4 | 3 | 1 | 9 | 8 | 1 | 84.62% |
| 9.7 | 1 | 4 | 3 | 1 | 9 | 8 | 1 | 84.62% |
| 9.8 | 1 | 4 | 3 | 1 | 9 | 8 | 1 | 84.62% |
| 9.9 | 1 | 4 | 3 | 1 | 9 | 8 | 1 | 84.62% |
| 10.0 | 1 | 4 | 3 | 1 | 9 | 8 | 1 | 84.62% |
| 10.1 | 1 | 4 | 3 | 1 | 9 | 8 | 1 | 84.62% |
| 10.2 | 1 | 4 | 3 | 1 | 9 | 8 | 1 | 84.62% |
| 10.3 | 1 | 4 | 3 | 1 | 9 | 8 | 1 | 84.62% |
| 10.4 | 1 | 4 | 3 | 1 | 9 | 8 | 1 | 84.62% |
| 10.5 | 1 | 4 | 3 | 1 | 9 | 8 | 1 | 84.62% |
| 10.6 | 1 | 4 | 3 | 1 | 9 | 8 | 1 | 84.62% |
| 10.7 | 1 | 4 | 3 | 1 | 9 | 8 | 1 | 84.62% |
| 10.8 | 1 | 4 | 3 | 1 | 9 | 8 | 1 | 84.62% |
| 10.9 | 1 | 4 | 3 | 1 | 9 | 8 | 1 | 84.62% |
| 11.0 | 1 | 4 | 3 | 1 | 9 | 8 | 1 | 84.62% |
| 11.1 | 1 | 4 | 3 | 1 | 9 | 8 | 1 | 84.62% |
| 11.2 | 1 | 4 | 3 | 1 | 9 | 8 | 1 | 84.62% |
| 11.3 | 1 | 4 | 3 | 1 | 9 | 8 | 1 | 84.62% |
| 11.4 | 1 | 4 | 3 | 1 | 9 | 8 | 1 | 84.62% |
| 11.5 | 1 | 4 | 3 | 1 | 9 | 8 | 1 | 84.62% |
| 11.6 | 1 | 4 | 3 | 1 | 9 | 8 | 1 | 84.62% |
| 11.7 | 1 | 4 | 3 | 1 | 9 | 8 | 1 | 84.62% |
| 11.8 | 1 | 4 | 3 | 1 | 9 | 8 | 1 | 84.62% |
| 11.9 | 1 | 4 | 3 | 1 | 9 | 8 | 1 | 84.62% |
| 12.0 | 1 | 4 | 3 | 1 | 9 | 8 | 1 | 84.62% |
| 12.1 | 1 | 4 | 3 | 1 | 9 | 8 | 1 | 84.62% |
| 12.2 | 1 | 4 | 3 | 1 | 9 | 8 | 1 | 84.62% |
| 12.3 | 1 | 4 | 3 | 1 | 9 | 8 | 1 | 84.62% |
| 12.4 | 1 | 4 | 3 | 1 | 9 | 8 | 1 | 84.62% |
| 12.5 | 1 | 4 | 3 | 1 | 9 | 8 | 1 | 84.62% |
| 12.6 | 1 | 4 | 3 | 1 | 9 | 8 | 1 | 84.62% |
| 12.7 | 1 | 4 | 3 | 1 | 9 | 8 | 1 | 84.62% |
| 12.8 | 1 | 4 | 3 | 1 | 9 | 8 | 1 | 84.62% |
| 12.9 | 1 | 4 | 3 | 1 | 9 | 8 | 1 | 84.62% |
| 13.0 | 1 | 4 | 3 | 1 | 9 | 8 | 1 | 84.62% |
| 13.1 | 1 | 4 | 3 | 1 | 9 | 8 | 1 | 84.62% |
| 13.2 | 1 | 4 | 3 | 1 | 9 | 8 | 1 | 84.62% |
| 13.3 | 1 | 4 | 3 | 1 | 9 | 8 | 1 | 84.62% |
| 13.4 | 1 | 4 | 3 | 1 | 9 | 8 | 1 | 84.62% |
| 13.5 | 1 | 4 | 3 | 1 | 9 | 8 | 1 | 84.62% |
| 13.6 | 1 | 4 | 3 | 1 | 9 | 8 | 1 | 84.62% |
| 13.7 | 1 | 4 | 3 | 1 | 9 | 8 | 1 | 84.62% |
| 13.8 | 1 | 4 | 3 | 1 | 9 | 8 | 1 | 84.62% |
| 13.9 | 1 | 4 | 3 | 1 | 9 | 8 | 1 | 84.62% |
| 14.0 | 1 | 4 | 3 | 1 | 9 | 8 | 1 | 84.62% |

TABLE 3-continued

Dispersion Test Parameters Yielding Optimal Performance
for 13-Patient Data Set Where Apnea-Hypopnea Index
(AHI) >= 13 Indicates Sickness

| Sub-Threshold Criteria % | # cubes | Apnea Pats. | De-tects | False Neg. | Normal Pats. | Correct Dismiss. | False Pos. | Success Rate |
|---|---|---|---|---|---|---|---|---|
| 14.1 | 1 | 4 | 3 | 1 | 9 | 8 | 1 | 84.62% |
| 14.2 | 1 | 4 | 3 | 1 | 9 | 8 | 1 | 84.62% |
| 14.3 | 1 | 4 | 3 | 1 | 9 | 8 | 1 | 84.62% |

Hardware for Identifying Sleep Apnea

The signal processing hardware is a USB client device that interfaces a nasal cannula to the host USB port on a personal computer. The device measures the nasal air pressure of a patient connected via a cannula. The air pressure is converted into an electrical signal, digitized and transferred over the USB interface to the host for processing.

Figure 9:
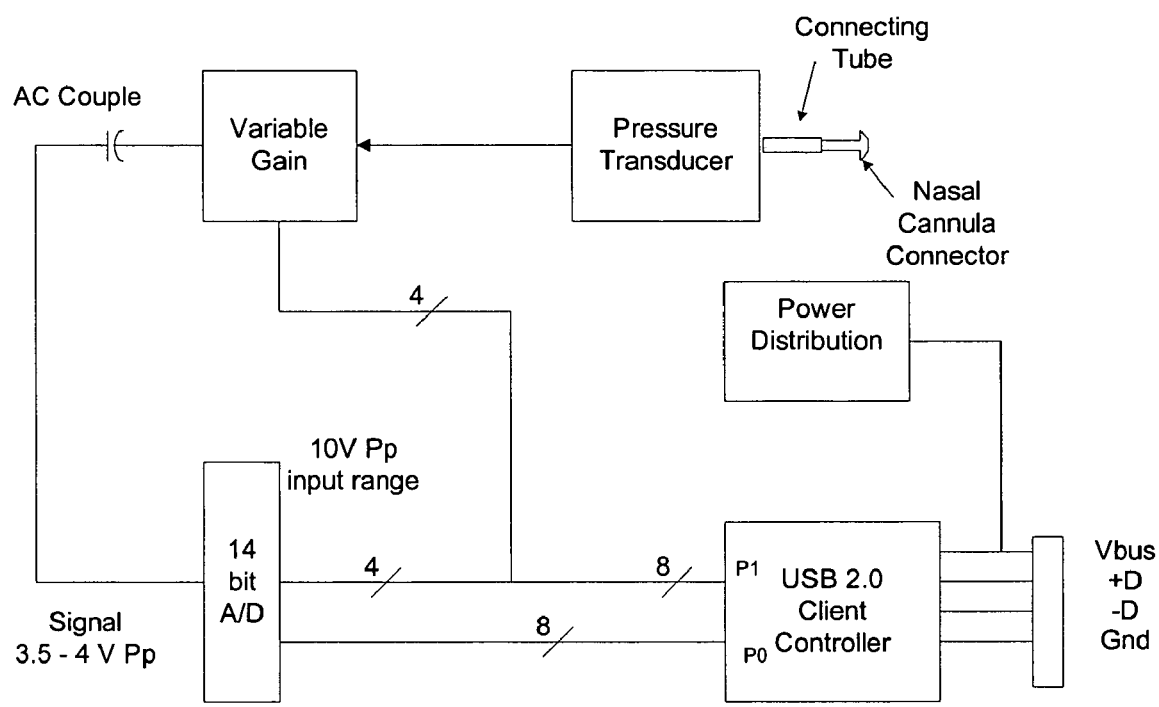
FIG. 9 is a block diagram representing the apparatus of the present invention; and, FIG. 10 is a diagram of the hardware platform of the present invention.

FIG. 9 illustrates the major functional blocks of the signal processing hardware. The Pressure Transducer converts the applied nasal air pressure into an analog electrical signal. The Variable Gain increases or decreases the maximum signal amplitude to about 2 Volts peak. (4 V Peak to Peak, Pp). The A/D Converter digitizes the analog signal into 14-bit sign plus magnitude word. Finally, the USB Controller is the external interface and controller for the client side of the Universal Serial Bus.

Figure 10:
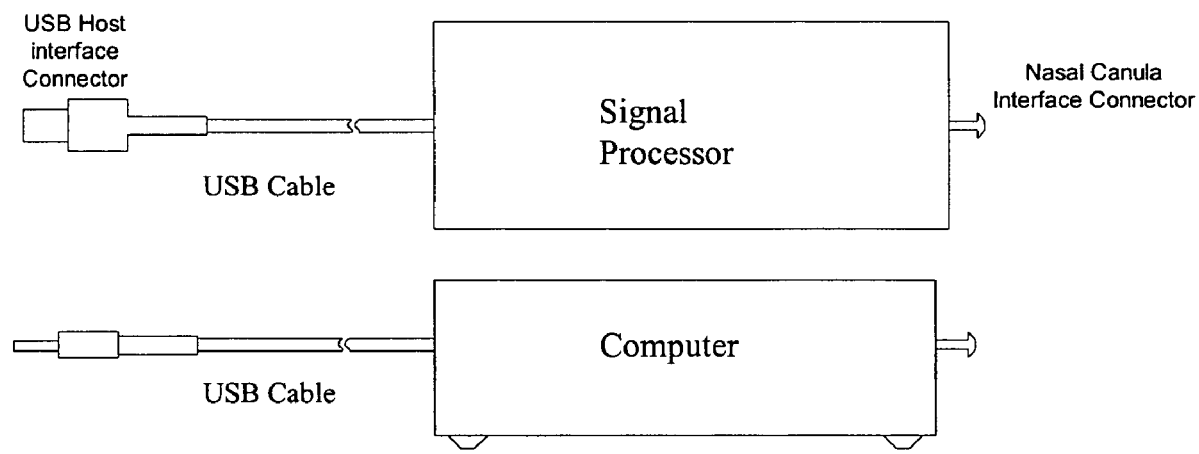

FIG. 10 illustrates the hardware platform of the present invention. The signal processing electronics were housed in a 7×5×3 inch plastic box with a USB cable extending from one end and the nasal cannula interface connector on the other. On the top surface of the device is a manual gain control button (not shown) for adjusting the output signal strength of the pressure transducer.

The platform consists of the signal processing hardware described above and a laptop personal computer. The computer hosts application software which controls the data collection (digitized nasal air pressure) and execution of the software algorithm. The signal processing hardware and laptop communicate via the USB port.

While the instant invention has been shown and described herein in what are conceived to be the most practical and preferred embodiments, it is recognized that departures, modifications, adaptations and variations may be made therefrom within and without departing from the scope of the invention, which is therefore not to be limited to the details disclosed herein, but also embraces any and all equivalent apparatus and articles.

What is claimed is:

1. A method for identifying a disease of a patient, the method comprising:
    collecting data of at least one cardio-respiratory function of the patient over time;
    eliminating artifacts from the collected data to create a new data record;
    constructing a phase-space from the new data record;
    constructing a hypercube covering the phase-space;
    calculating threshold criteria for quantifying dispersion characteristics of an attractor of the phase-space; and
    determining the patient's tendency towards the disease based on the threshold criteria and the hypercube.

2. The method of claim 1, wherein collecting data is performed while the patient is awake.

3. The method of claim 2, wherein collecting data includes measuring nasal pressure.

4. The method of claim 1, wherein eliminating artifacts includes normalizing the collected data.

5. The method of claim 4, wherein the collected data outside a threshold range are eliminated.

6. The method of claim 5, further including replacing the eliminated data with a linear interpolation of data within the threshold range.

7. The method of claim 1, wherein constructing the phase-space includes creating a multi-dimensional set of vectors.

8. The method of claim 7, wherein creating the set of vectors includes selecting a delay parameter and an embedding dimension.

9. The method of claim 1, wherein the hypercube includes a plurality of mini-cubes, the plurality of mini-cubes being non-overlapping and each mini-cube being of substantially equal proportion.

10. The method of claim 9, wherein the plurality of mini-cubes identify the highest density region of data within the phase-space.

11. The method of claim 10, wherein the plurality of mini-cubes quantify dispersive characteristics of the attractor.

12. The method of claim 11, wherein the plurality of mini-cubes quantify the shape of the attractor.

13. The method of claim 1, wherein calculating the threshold criteria includes using the new data record to calculate the threshold criteria.

14. The method of claim 13, wherein calculating the threshold criteria includes calculating a minimum acceptable percentage of a number of data that pass through a specific mini-cube of the hypercube with respect to the number of data that pass through a mini-cube having the maximum density of data.

15. The method of claim 14, wherein calculating the threshold criteria further includes counting the minimum number of mini-cubes for the minimum acceptable percentage.

16. The method of claim 15, wherein a lower threshold criteria indicates a tendency toward the patient having the disease.

17. A method for identifying a disease of a patient, the method comprising:
    collecting data of at least one cardio-respiratory function of the patient over time;
    constructing a first phase-space from the collected data;
    calculating differential radii of the collected data in the first phase-space;
    determining a threshold crossing level;
    calculating a percentage of differential radii exceeding the threshold crossing level;
    preliminarily determining the patient's tendency towards the disease based on the percentage of differential radii;
    eliminating artifacts from the collected data to create a new data record;
    constructing a second phase-space from the new data record;
    constructing a hypercube covering the second phase-space;

calculating threshold criteria for quantifying dispersion characteristics of an attractor of the second phase-space; and determining the patient's tendency towards the disease based on the threshold criteria and the hypercube.

18. The method of claim 17, wherein the disease is one of Sudden Infant Death Syndrome, Apparent Life Threatening Event, sleep disordered breathing, respiratory disease, cardiac disease, cardio-respiratory disease, and neurological disease.

19. The method of claim 17, wherein collecting data includes collecting at least one of nasal pressure, nasal temperature, chest-wall expansion and contraction, abdomen expansion and contraction, electrocardiogram (ECG), electroencepthalogram (EEG), electromyography (EMG).

20. The method of claim 17, wherein collecting data is performed while the patient is awake.

* * * * *